United States Patent [19]

Anderson

[11] Patent Number: 5,521,653
[45] Date of Patent: May 28, 1996

[54] VISION RESTRICTING SPORTS TRAINING GLASSES

[76] Inventor: Paul A. Anderson, Autec Andros Ranges, P.O. Box 374, PSC 1012, Fla. 34058

[21] Appl. No.: 251,237

[22] Filed: May 31, 1994

[51] Int. Cl.⁶ .................................................... G02C 7/16
[52] U.S. Cl. ............................ 351/45; 351/46; 351/156
[58] Field of Search ............................ 273/1.5 A, 260, 273/29 A, 190 A, 190 R, 55 R, 57.2, DIG. 17; 2/13, 425, 433, 434, 440, 441, 442, 443, 445, 446, 452; D16/311, 339; 351/41, 43, 45, 47, 44, 57, 59, 62, 123, 130, 156, 158

[56] References Cited

U.S. PATENT DOCUMENTS

| | | | |
|---|---|---|---|
| 1,095,543 | 5/1914 | Barr | 351/47 |
| 1,308,484 | 7/1919 | Day | 2/441 |
| 2,504,524 | 4/1950 | Hayward | 351/156 X |
| 2,526,582 | 10/1950 | Rowan | 351/59 X |
| 3,628,854 | 12/1971 | Jampolsky | 351/45 X |
| 4,022,475 | 5/1977 | Todd | 2/13 X |
| 4,991,849 | 2/1991 | Fabanich | 351/45 X |
| 5,177,510 | 1/1993 | Peters et al. | 351/45 |

Primary Examiner—William L. Sikes
Assistant Examiner—Hung Xuan Dang

[57] ABSTRACT

Sports training glasses for restricting an individual's field of vision. The inventive device includes a forehead strap and an overhead strap positionable upon the head of the individual, with a nose strap extending downwardly from the forehead strap to support a nose piece. A pair of ocular pads are coupled to opposed sides of the nose piece and are each configured to encompass the ocular cavity, with a pair of temple straps extending from the pads about the head. A plurality of restrictive lenses are attachable to the ocular pads and include different field of view limiting apertures including a horizontal aperture, a square aperture, a circular aperture, and a triangular aperture, with each aperture shape corresponding to a particular desired sport, such as football, hockey, basketball, baseball, and the like.

12 Claims, 3 Drawing Sheets

5,521,653

VISION RESTRICTING SPORTS TRAINING GLASSES

BACKGROUND OF THE INVENTION

1. Field of the Invention

The present invention relates to glasses and more particularly pertains to vision restricting sports training glasses for restricting an individual's field of vision.

2. Description of the Prior Art

The use of glasses is known in the prior art. More specifically, glasses heretofore devised and utilized for the purpose of restricting vision are known to consist basically of familiar, expected and obvious structural configurations, notwithstanding the myriad of designs encompassed by the crowded prior art which have been developed for the fulfillment of countless objectives and requirements.

For example, alignment eyeglasses are illustrated in U.S. Pat. No. 5,177,510 which may be utilized to aid a wearer, especially athletes or participants in sports, to diminish the input from his oculo-vestibular reflexes and provide immediate visual feedback concerning alignment. The eyeglasses have one or more substantially straight, visible transparent lines on one or both of the eye pieces which appear to be superimposed on the view through the line or lines. The lines enable the wearer of the eyeglasses to readily check alignment of the body, head, hands, and/or a held object with a viewed object, e.g. a golf ball, a pitched baseball, a bowling pin, a basketball, etc.

Other known prior art glasses are disclosed in U.S. Pat. Nos. 4,741,611; 4,953,967; 5,162,823; 5,076,681; and U.S. Pat. No. Des. 273,684.

While these devices fulfill their respective, particular objectives and requirements, the aforementioned patents do not disclose vision restricting sports training glasses for restricting an individual's field of vision which include a forehead strap and an overhead strap positionable upon the head of the individual, with a nose strap extending downwardly from the forehead strap to support a nose piece, and a pair of ocular pads coupled to opposed sides of the nose piece, with the ocular pads each being operable to support a vision restricted lens in front of the individual's eye. Furthermore, none of the known prior art glasses teach or suggest vision restricting sports training glasses of the aforementioned structure which further include restrictive lenses having different field of view limiting apertures including a horizontal aperture, a square aperture, a circular aperture, and a triangular aperture, with each aperture shape corresponding to a particular desired sport, such as football, hockey, basketball, baseball, and the like.

In these respects, the vision restricting sports training glasses according to the present invention substantially departs from the conventional concepts and designs of the prior art, and in so doing provides an apparatus primarily developed for the purpose of restricting an individual's field of vision.

SUMMARY OF THE INVENTION

In view of the foregoing disadvantages inherent in the known types of glasses now present in the prior art, the present invention provides a new vision restricting sports training glasses construction wherein the same can be utilized for restricting individual's field of vision. As such, the general purpose of the present invention, which will be described subsequently in greater detail, is to provide a new vision restricting sports training glasses apparatus and method which has many of the advantages of the glasses mentioned heretofore and many novel features that result in a vision restricting sports training glasses which is not anticipated, rendered obvious, suggested, or even implied by any of the prior art glasses, either alone or in any combination thereof.

To attain this, the present invention generally comprises sports training glasses for restricting an individual's field of vision. The inventive device includes a forehead strap and an overhead strap positionable upon the head of the individual, with a nose strap extending downwardly from the forehead strap to support a nose piece. A pair of ocular pads are coupled to opposed sides of the nose piece and are each configured to encompass the ocular cavity, with a pair of temple straps extending from the pads about the head. A plurality of restrictive lenses are attachable to the ocular pads and include different field of view limiting apertures including a horizontal aperture, a square aperture, a circular aperture, and a triangular aperture, with each aperture shape corresponding to a particular desired sport, such as football, hockey, basketball, baseball, and the like.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide new vision restricting sports training glasses apparatus and method which has many of the advantages of the glasses mentioned heretofore and many novel features that result in a vision restricting sports training glasses which is not anticipated, rendered obvious, suggested, or even implied by any of the prior art glasses, either alone or in any combination thereof.

It is another object of the present invention to provide new vision restricting sports training glasses which may be easily and efficiently manufactured and marketed.

It is a further object of the present invention to provide new vision restricting sports training glasses which is of a durable and reliable construction.

An even further object of the present invention is to provide new vision restricting sports training glasses which is susceptible of a low cost of manufacture with regard to both materials and labor, and which accordingly is then susceptible of low prices of sale to the consuming public, thereby making such vision restricting sports training glasses economically available to the buying public.

Still yet another object of the present invention is to provide new vision restricting sports training glasses which provides in the apparatuses and methods of the prior art some of the advantages thereof, while simultaneously overcoming some of the disadvantages normally associated therewith.

Still another object of the present invention is to provide new vision restricting sports training glasses for partially restricting an individual's field of vision.

Yet another object of the present invention is to provide new vision restricting sports training glasses which include a forehead strap and an overhead strap positionable upon the head of an individual, with a nose strap extending downwardly from the forehead strap to support a nose piece, a pair of ocular pads coupled to opposed sides of the nose piece, a pair of temple straps extending from the pads about the head, and a plurality of restrictive lenses attachable to the ocular pads for restricting the individual's field of vision.

Even still another object of the present invention is to provide new vision restricting sports training glasses including restrictive lenses having different limiting apertures including a horizontal aperture, a square aperture, a circular aperture, and a triangular aperture, with each aperture shape corresponding to a particular desired sport, such as football, hockey, basketball, baseball, and the like.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
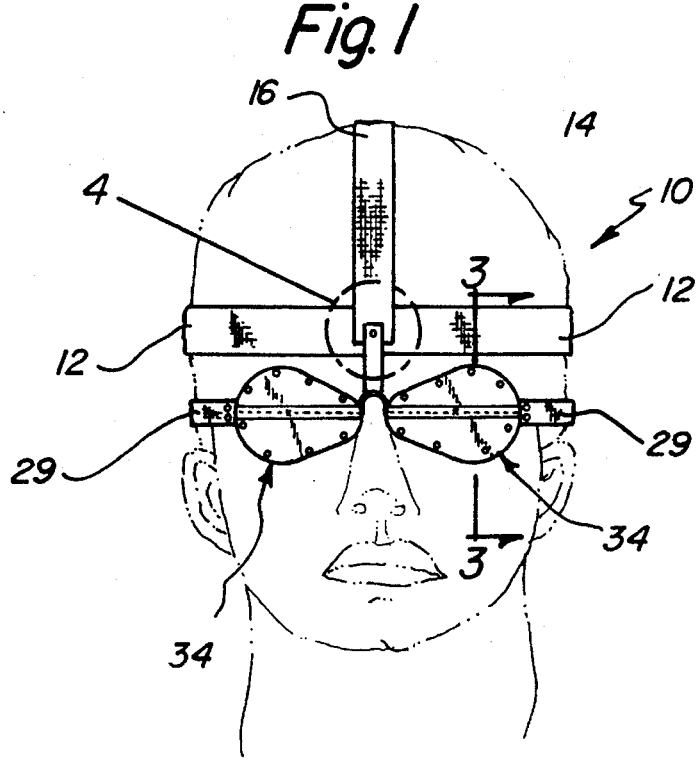
FIG. 1 is a front elevation view of vision restricting sports training glasses comprising the present invention as positioned upon the head of an individual.

With reference now to the drawings, and in particular to FIGS. 1–8 thereof, new vision restricting sports training glasses embodying the principles and concepts of the present invention and generally designated by the reference numeral 10 will be described.

Figure 2:
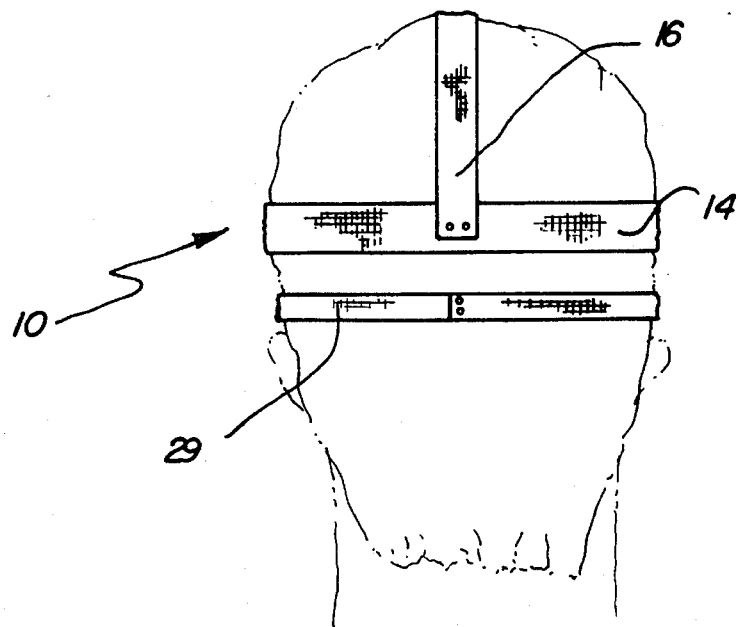
FIG. 2 is a rear elevation view of the present invention.
Figure 4:
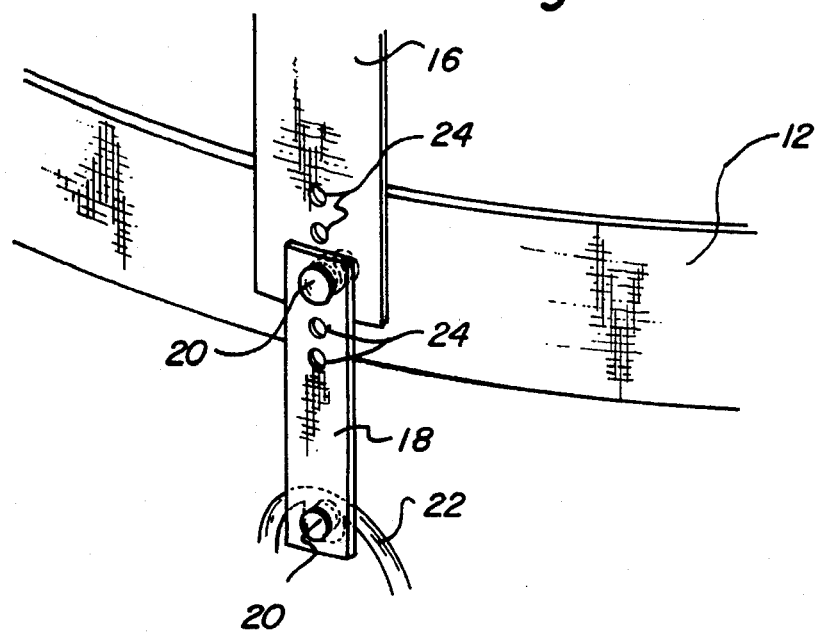
FIG. 4 is an enlarged isometric illustration of the area set forth in FIG. 1.

More specifically, it will be noted that the vision restricting sports training glasses 10 comprise a forehead strap 12 of elastic construction operable to be positioned about the forehead area of the head 14 of an individual wearing the glasses 10. An overhead strap 16 extends from a center of the forehead strap 12 over a center of the individual's forehead and over the head 14, whereat the overhead strap is coupled to a posterior center area of the forehead strap, as best illustrated in FIGS. 1 and 2. Thus, the forehead strap 12 is positioned within a substantially horizontal plane, while the overhead strap 16 lies in a substantially vertical plane. The straps 14, 16 are preferably formed of an absorbent material so as to additionally function as a sweatband. Extending from the anterior center area of the forehead strap 12 is a nose strap 18 which extends downwardly from the center of the forehead to a point just above the nose of the individual, as illustrated in FIGS. 1 and 4. The nose strap 18, as well as the overhead strap 16, are coupled to the forehead strap 12 by removable fasteners 20 such as threaded studs, snaps, buttons, or the like. Another removable fastener 20 further couples a lower distal end of the nose strap 18 to a nose piece wire 22 configured to straddle the individual's nose. To impart adjustability to the device 10, the overhead strap 16 and the nose strap 18 are provided with a plurality of adjustment apertures 24 through which the removable fasteners 20 may extend to couple the straps to the forehead strap 12. By this structure, the training glasses 10 may be fitted to a variety of disparate individuals.

Figure 3:
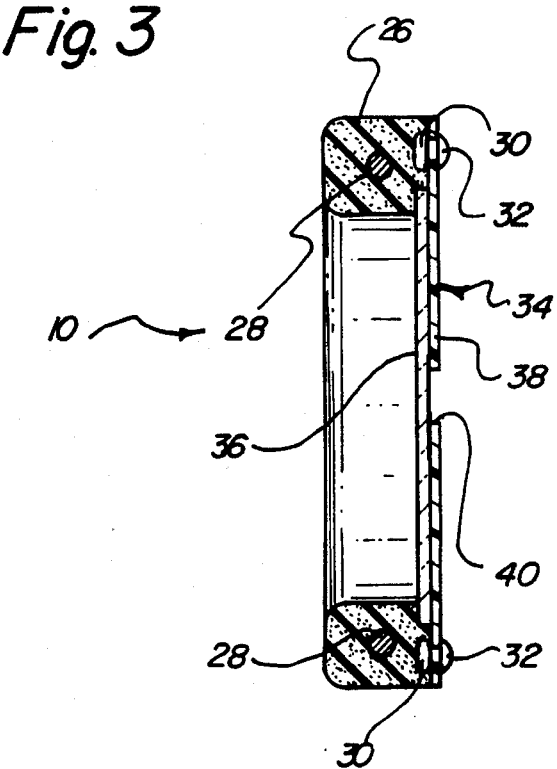
FIG. 3 is a cross sectional view taken along line 3—3 of FIG. 1.

Positioned on laterally opposed sides of the nose piece wire 22 are a pair of teardrop-shaped ocular pads 26 which substantially circumscribe the ocular cavity of the individual. Each of the ocular pads 26 is substantially identical in shape, and includes a shape retaining wire 28 extending therethrough, as best illustrated in FIG. 3. The ocular pads 26 are constructed of a substantially resilient foam material capable of creating a light-tight seal about the ocular cavity. To this end, the shape retaining wire 28 may be slightly deformed to further conform the ocular pads 26 to the facial area about the ocular cavity, whereby such deformation will be retained by the ductile nature of retaining wire. The shape retaining wire 28, in addition to the shape retaining function recited above, further serves as an internal frame for each of the ocular pads. The shape retaining wire 28 is coupled to the nose piece wire 22 to support each of the ocular pads over the respective left and right eyes of the individual, as illustrated in FIG. 1. To this end, the nose piece wire 22 and the shape retaining wire 28 may be single elongated piece of integral wire. In addition, and to further ensure a sealing of the ocular pads 26 about the ocular cavities of the individual, a temple strap 29 is secured to the outboard edges of the pads and extends about the head 14 of the individual, as illustrated in FIG. 2.

Positioned about a forward facing edge of each of the ocular pads 26 is a plurality of male snaps 30 which cooperate with a plurality of aligned female snaps 32 to removably secure a restrictive lens 34 to each of the ocular pads 26. The restrictive lenses 34 comprise a transparent glass 36 which may be a rigid glass material, or a flexible plastic material, with an exterior facia 38 laminated to a forward surface of the transparent glass. The exterior facia 38 may be a rigid plate member, or, alternatively, may be a flexible plate member such that a flexible plastic transparent glass 36 and a flexible exterior facia permit the restrictive lens 34 to be slightly deformed in conjunction with the shape retaining wire 28 deformation procedure described above to further conform the ocular pads 26 to the ocular cavity of the individual. Regardless of the rigid or flexible construction of the exterior facia 38, a facia aperture 40 is present near a center area of the transparent glass 36. The exterior facia 38 is preferably opaque, but may be slightly translucent to allow for some permeation of light therethrough. Conversely, the transparent glass 36 is preferably transparent, but may be substantially translucent or tinted such that light passing therethrough is slightly modified. In addition, the transparent glass 36 may comprise a vision corrective lens such that contact lenses need not be utilized with the device 10.

Figure 5:
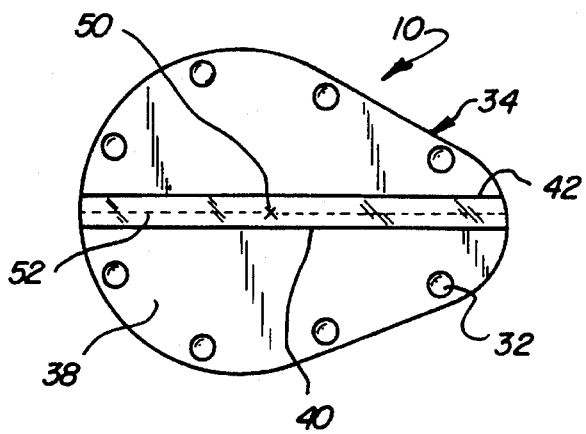
FIG. 5 is a front elevation view of a restricted lens having an elongated, horizontal aperture.

Turning now to FIGS. 5 through 8, it can be shown that the restrictive lenses 34 may include facia apertures 40 of various shapes. To this end, the restrictive lens 34 illustrated in FIG. 5 includes an elongated, horizontal aperture 42 useful during training for the sport of football, such as by a quarterback, or the like, for eliminating from the field of view the interaction of the front linesmen, which could distract the quarterback from the pass receivers downfield. In addition, the elongated horizontal aperture 42 of the restrictive lens 34 illustrated in FIG. 5 is useful during the reading of a book or other printed material by permitting the visualization of a single line of text at a one time.

Figure 6:
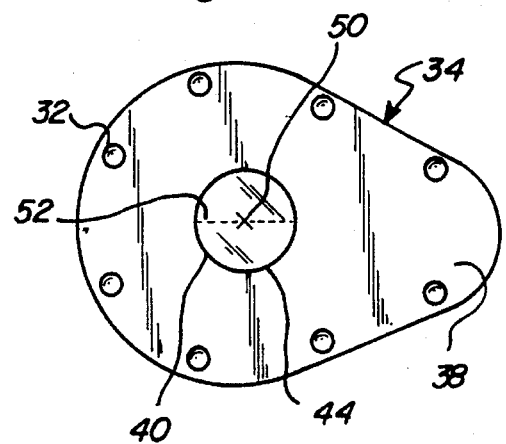
FIG. 6 is a front elevation view of a restrictive lens having a circular aperture.

FIG. 6 illustrates a restrictive lens 34 having a circular aperture 44 which may be utilized during training for the sport of basketball by restricting the individual's field of vision to the basketball hoop during a shooting procedure or the like. Thus, the individual practicing the sport of basketball while wearing the training glasses 10 is required to consistently position the head 14 at a specific orientation to visualize the basketball hoop through the circular aperture 44 each time a shot is made.

Figure 7:
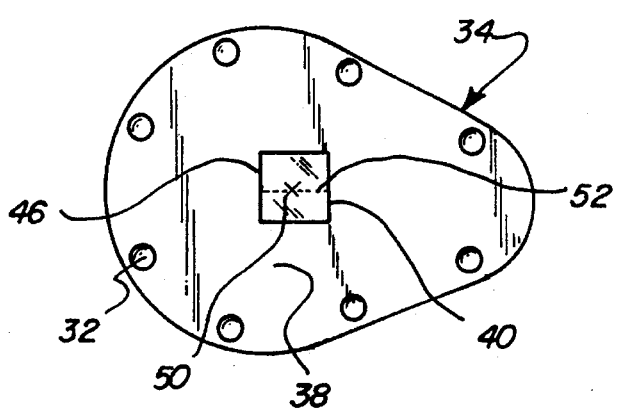
FIG. 7 is a front elevation view of a restrictive lens having a square aperture.

FIG. 7 illustrates a restrictive lens 34 including a square aperture 46 which, in a manner similar to that of the circular aperture 44, requires the individual to position the head 14 in a consistent manner during shooting of a puck or the like into a hockey or soccer goal, with the square aperture corresponding to the shape of such goal.

Figure 8:
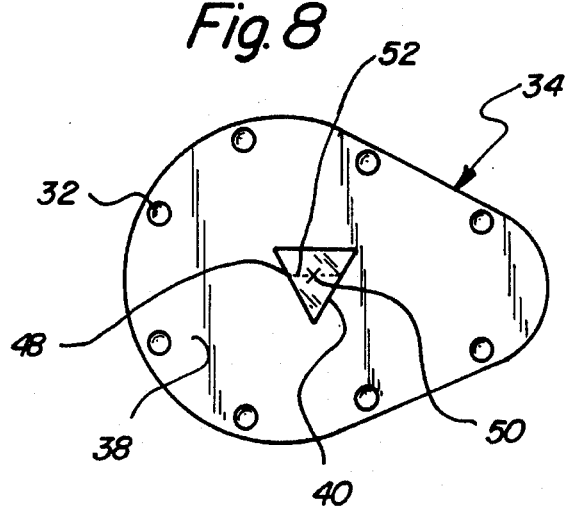
FIG. 8 is a front elevation view of a restrictive lens having a triangular aperture.

FIG. 8 depicts a restrictive lens including a triangular aperture 48 useful during practice and playing of the sport of baseball. To this end, the triangular aperture 48 substantially corresponds to the shape of a baseball diamond and restricts the individual's field of view to the diamond to effectively exclude distractions such as laterally positioned crowds and the like. Further, the triangular aperture 48 is useful during practice and play of the sport of bowling by substantially restricting the individual's field of vision to the triangularly arranged pins at the end of the bowling alley.

In addition, and regardless of the shape of the facia aperture 40, the restrictive lenses 34 are provided with center indicia 50 in the form of a "X" which provides a reference point for further ensuring that a consistent positioning of the individual's head 14 is obtained during practice and play of any of the aforementioned sports. Further, horizontal alignment indicia 52 is provided as a reference point upon which to judge tilting and swaying of the individual's head 14, such that upon becoming aware of such tilting, the individual may practice and train to eliminate such swaying and tilting.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. Vision restricting sports training glasses comprising:
    a nose piece wire configured to straddle a nose of an individual;
    means for supporting said nose piece wire upon said nose of said individual;
    a pair of ocular pads coupled to laterally opposed sides of said nose piece wire, said pads each having an outer later side, each of said ocular pads including a ductile, shape retaining wire extending therethrough, such that said shape retaining wire is deformable to conform the ocular pads to the facial area about the ocular cavity of the individual, whereby such deformation will be retained by the ductile nature of retaining wire; and;
    a pair of restrictive lenses removably coupled to said pads for restricting a peripheral vision of the individual, said restrictive lenses comprising a transparent glass and an exterior facia having a facia aperture extending therethrough, said exterior facia being coupled to said transparent glass.

2. The vision restricting sports training glasses of claim 1, wherein said restrictive lenses further comprise horizontal alignment indicia on said transparent glass.

3. The vision restricting sports training glasses of claim 2, wherein said restrictive lenses further comprise center indicia on said glass, said center indicia being positioned in a center of said facia aperture.

4. The vision restricting sports training glasses of claim 3, wherein said facia aperture is shaped so as to define an elongated horizontal aperture.

5. The vision restricting sports training glasses of claim 3, wherein said facia aperture is shaped so as to define a circular aperture.

6. The vision restricting sports training glasses of claim 3, wherein said facia aperture is shaped so as to define a square aperture.

7. Vision restricting sports training glasses comprising:
    a forehead strap for encompassing a head of an individual, said forehead strap having an anterior center area and a posterior center area;

an overhead strap extending from said anterior center of said forehead strap to said posterior area of said forehead strap, with said forehead strap being substantially orthogonally oriented relative to said overhead strap such that said overhead strap extends over the head of the individual;

a nose strap extending downwardly from said anterior center of said forehead strap, said nose strap having a lower distal end;

a nose piece wire attached to said lower distal end of said nose strap, said nose piece wire being configured to straddle a nose of the individual;

a pair of teardrop shaped ocular pads coupled to laterally opposed sides of said nose piece wire, said pads each having an outer lateral side;

a temple strap extending from said outer lateral sides of said pads for encompassing said head of said individual;

and;

a pair of restrictive lenses removably coupled to said pads for restricting a peripheral vision of the individual, said restrictive lenses comprising a transparent glass, and an exterior facia having a facia aperture extending therethrough, said exterior facia being coupled to said glass, with said glass having center indicia thereon positioned in a center of said facia aperture.

8. The vision restricting sports training glasses of claim 7, wherein said restrictive lenses further comprise horizontal alignment indicia on said transparent glass.

9. The vision restricting sports training glasses of claim 8, wherein each of said ocular pads includes a ductile, shape retaining wire extending therethrough, such that said shape retaining wire is deformable to conform the ocular pads to the facial area about the ocular cavity of the individual, whereby such deformation will be retained by the ductile nature of retaining wire.

10. The vision restricting sports training glasses of claim 9, wherein said facia aperture is shaped so as to define an elongated horizontal aperture.

11. The vision restricting sports training glasses of claim 9, wherein said facia aperture is shaped so as to define a circular aperture.

12. The vision restricting sports training glasses of claim 9, wherein said facia aperture is shaped so as to define a square aperture.

* * * * *